United States Patent [19]

Van Pool et al.

[11] Patent Number: 4,476,097
[45] Date of Patent: Oct. 9, 1984

[54] RELIEF SYSTEM

[75] Inventors: Joe Van Pool; Mack F. Potts, both of Bartlesville, Okla.

[73] Assignee: Phillips Petroleum Co., Bartlesville, Okla.

[21] Appl. No.: 424,801

[22] Filed: Sep. 27, 1982

Related U.S. Application Data

[62] Division of Ser. No. 296,948, Aug. 28, 1981, Pat. No. 4,409,420.

[51] Int. Cl.³ .................... B01J 10/00; G05D 16/00
[52] U.S. Cl. .................... 422/112; 422/113; 422/115; 422/117; 422/169; 423/240; 423/241
[58] Field of Search ............. 422/112, 113, 115, 117, 422/169; 423/240, 241; 585/723

[56] References Cited

U.S. PATENT DOCUMENTS

| | | | |
|---|---|---|---|
| 2,773,920 | 12/1956 | Vautrain et al. | 585/723 |
| 2,792,070 | 5/1957 | Strunk | 55/20 |
| 2,988,894 | 6/1961 | Van Pool et al. | 62/28 |
| 3,158,661 | 11/1964 | Plaster et al. | 585/723 X |
| 3,206,390 | 9/1965 | Van Pool | 585/723 X |
| 3,972,956 | 8/1976 | Carter | 585/331 |
| 4,009,221 | 2/1977 | Carter | 585/723 |

Primary Examiner—Michael Marcus
Attorney, Agent, or Firm—Howard D. Doescher

[57] ABSTRACT

Hydrocarbon vapors containing HF, as from an HF alkylation refrigerated vent gas yield, the reactor settler, and the like are charged to a liquid knock-out drum to remove entrained liquid therefrom, the recovered liquid being pumped to storage in response to liquid level control on the knock-out drum. Recovered vapors are charged to a circulating aqueous caustic treater to yield HF-free vapors, as to a flare. The circulating caustic solution is indirectly heated in response to a preselected caustic solution temperature to prevent freezing. A high pressure rupture disc, upstream from the knock-out drum, affords a vapor relief safety by-pass of the treater. Dry gas, such as nitrogen or sweet, natural gas, continuously sweeps the relief line to maintain this line open and operable.

6 Claims, 1 Drawing Figure

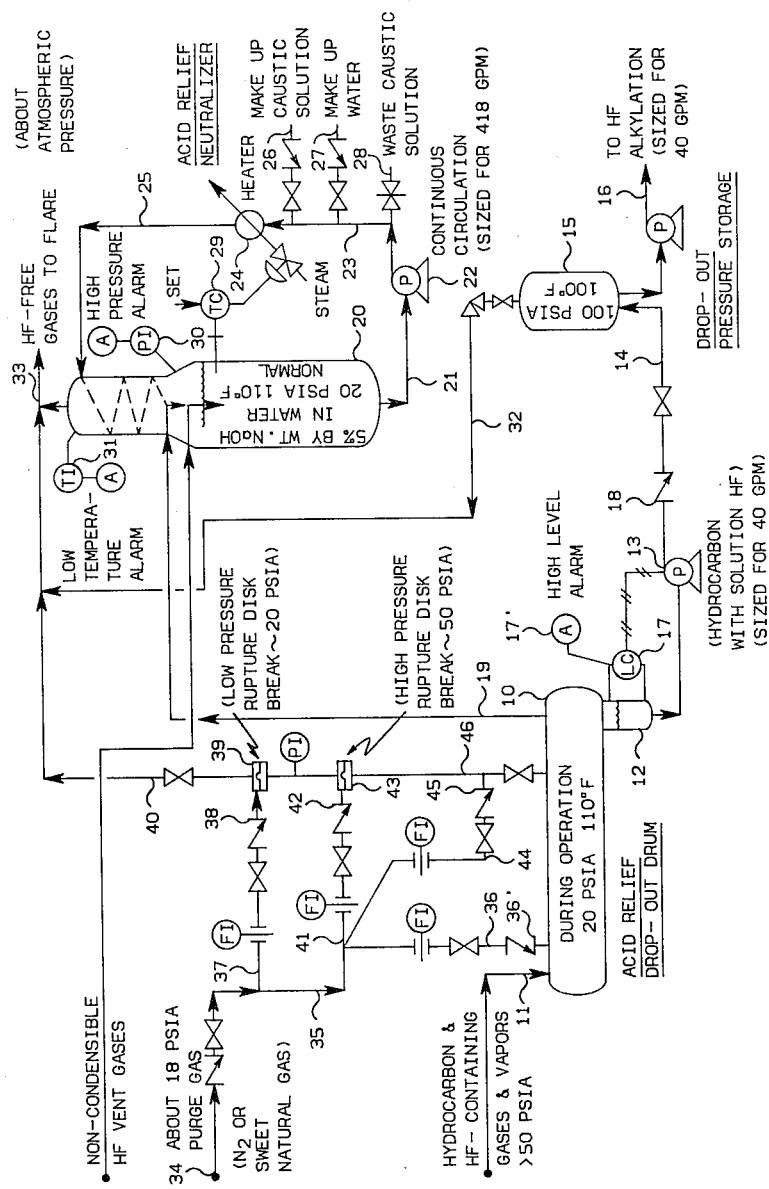

4,476,097

RELIEF SYSTEM

This application is a divisional application of my co-pending application, Ser. No. 296,948 filed Aug. 28, 1981 now U.S. Pat. No. 4,409,420, issued Oct. 11, 1983.

FIELD OF INVENTION

This invention relates to fluids handling. In accordance with another aspect, this invention relates to a relief system for handling an acid-hydrocarbon vaporous or gaseous stream. In accordance with a further aspect, this invention relates to a relief system for handling HF acid-hydrocarbon vapors utilizing an aqueous neutralizing treatment step and a vapor relief safety system to prevent explosive situations developing. In accordance with a further aspect, this invention relates to a combination system comprising an acid relief drop-out vessel or zone, high and low pressure rupture discs, and a neutralizing treating zone, all connected to a relief and flare system.

BACKGROUND OF INVENTION

In the operation of a process such as HF catalytic alkylation of isobutane with propylene and/or butylenes, relief gases containing HF and light hydrocarbons, such as from the HF catalyst storage tank, the reactor settler, the product hydrocarbon-HF recontactors, the depropanizer refrigerated overhead accumulator, and the like, cannot be vented or sent to the flare because of ecologic problems with HF. HF passes through the flare unchanged.

This HF must be removed from these streams in order to minimize corrosion in the relief lines, as to the flare and to minimize atmospheric pollution.

This invention employs an HF acid relief drop-out drum to accumulate and remove any liquid hydrocarbons present in the relief fluids or produced in the system, as by condensation of the light hydrocarbon vapors. This liquid removal protects the acid relief neutralizer vessel in that, under normal operating conditions, substantially only non-condensible hydrocarbons containing HF are charged to the neutralizer. When, under upset operations liquid hydrocarbon, such as propane, enters the neutralizer, evaporation of the propane can cause freeze-up of even the caustic solution, resulting in high pressure build up in this system with disastrous results. High pressure can rupture the vessels and fire and explosion can result from the released hydrocarbons.

Purge gas, such as nitrogen or sweet (sulfur-free) fuel gas, as for example natural gas, is applied to the system. When there are no relief gases charged to the operation, the purge gas sweeps through the drop-out drum and the neutralizer to prevent moisture from entering the system, e.g., via the flare unit, due to temperature changes, e.g., night-time cooling drawing in moist air. The moisture entering can dissolve HF forming corrosive liquid which can damage piping and vessels of the system. The purge gas prevents this problem. Purge gas also passes continuously through the by-pass line around the neutralizer.

In order to provide greater safety, it has occurred to me that heating of the circulating neutralizing agent and the provision of a vapor relief safety by-pass of the neutralizing zone, which has a high pressure rupture disc, would provide such additional safety which would avoid the hazards of a disastrous explosion.

Accordingly, an object of this invention is to provide a method and means for fluids handling.

Another object of this invention is to provide a means for preventing explosions in a fluids handling system.

A further object of this invention is to provide an improved knock-out drum-caustic treating system in an HF acid alkylation operation.

Other aspects, objects, and the several advantages of this invention are apparent from the study of this disclosure, drawing, and the appended claims.

SUMMARY OF THE INVENTION

According to the present invention, which will now be described with respect to an HF-alkylation operation, hydrocarbon vapors containing HF are charged to a liquid knock-out drum to remove entrained liquid therefrom and the recovered vapors are charged to a circulating neutralizing treater zone to yield HF-free vapors, for example to a flare. The circulating neutralizing agent, for example caustic solution, is indirectly heated in response to a preselected caustic solution temperature to prevent freezing in the neutralizing zone. In a preferred embodiment, a high pressure rupture disc, located upstream from the knock-out drum, affords a vapor relief safety by-pass of the neutralizing treater. A dry inert gas, such as nitrogen or sweet, natural gas, continuously sweeps the relief line to maintain this line open and operable.

DETAILED DESCRIPTION OF THE INVENTION

Referring to the drawing which will now be described, one skilled in the art will understand that operations other than that to be desired in connection with the drawing can be effected in an operation or means substantially like that to be described. Thus, the invention is broadly applicable to other than HF acid alkylation vapors disposal or treatment. As one skilled in the art knows, there are various operations involved in petroleum refining and generally in the chemical or petrochemical arts.

In the drawing, 10 and 20 are respectively an acid relief drop-out drum and an acid relief neutralizer. HF acid in hydrocarbon vapors enters drop-out drum 10 by way of line 11. These vapors result from pressure relief valves variously placed within the HF alkylation operation.

Knock-out or drop-out drum 10 is usually operated slightly above or near ambient temperature and slightly elevated pressure and therein will be formed a liquid phase which is recovered by way of line 12 and returned to the system as to the alkylation feed by pump 13, pipe 14, storage vessel 15, and line 16. Pump 13 is controlled by liquid level controller 17, with high level alarm 17'. There is also provided a check valve 18 in line 14, to prevent flow from vessel 15 back into conduit 12.

Vapors are removed from drop-out drum 10 by way of line 19 and pass to acid relief neutralizer 20 wherein the vapors are scrubbed while passing upwardly through vessel 20 by a neutralizing agent, such as a caustic (NaOH) solution, passing downwardly through neutralizer 20. Neutralizer 20 can be provided with suitable contacting elements, such as perforated plates, etc.

Neutralizing agent solution is removed from a lower portion of vessel 20 by line 21, passed through pump 22, line 23, heater 24, line 25, and returned to an upper portion of neutralizer 20. Make-up caustic or neutralizing agent can be added as desired by pipe 26. Similarly, make-up water can be added by way of line 27 and waste caustic withdrawn from the system by way of line 28.

The neutralizing agent solution, circulated from a lower portion of neutralizer 20 to an upper portion of neutralizer 20, is passed through heater 24 which is controlled by temperature controller 29 to maintain the desired temperature for the circulating treating agent to prevent freeze-up within neutralizer 20 in the event of excessive evaporation of light hydrocarbons within the vessel. Neutralizer 20 is provided with a high pressure alarm 30 and a low temperature alarm 31.

Vapors carried into storage 15 can be vented by way of line 32 and passed to flare (not shown) by way of line 33.

An inert gas, such as nitrogen or a sweet, natural gas, is introduced into the system by way of line 34, then passed by way of line 35 and valved line 36, and check valve 36', and introduced into drop-out drum 10. Another portion of the inert gas can be passed by way of line 37, through check valve 38, and introduced into the downstream side of a low pressure rupture disc 39 and, thence, through line 40 for connection with line 33 and passage to a flare. By so operating, an inert gas is continually passed through the relief by-pass line 40 to prevent moisture from entering the system.

Another portion of the inert gas is passed by way of line 41, check valve 42, and into the downside stream of a high pressure rupture disc 43. A further portion of inert gas is passed by way of line 44 and check valve 45 and introduced into line 46 connecting the upstream side of high pressure rupture disc 43 and drop-out drum 10.

OPERATION OF THE SYSTEM

When there is no flow of relief gases into the acid relief drop-out drum and when only purge gas is flowing into the drum, the pressure in the drum is relatively low, just a few inches of water pressure above atmospheric pressure, e.g., 1 to 2 inches water, gauge.

The purge gas pressure is relatively low, e.g., 2 to 5 psig, e.g., 3 psig.

When there is no flow of relief gases and only purge gas flow and when the high pressure disc and low pressure disc are both intact, the pressure between the two discs will read about 3 psig (purge gas pressure).

If either disc is leaking, or if both discs are leaking, and there is no flow of relief gases, but only flow of purge gas, the pressure between the two discs will be low, e.g., about 1 to 2 inches water gauge (just sightly above atmospheric pressure).

When the system is receiving vent gases, which can be up to even 300 psia, the pressure within the drop-out drum reaches only about 5 psig. [This is true because the drop-out drum is in "very" open flow communication with the tray section of the acid relief neutralizer which is in open communication with the flare (at about atmospheric presure)]. During this flow of relief gases, no purge gas can enter the drop-out drum (check valve prevents relief gas flow back into purge system). Purge gas, however, still flows via the by-pass conduit and maintains about 3 psig in the zone between the two discs, when the discs are intact. Should the lower disc be leaking during relief gas flow, the pressure between the discs will be about 5 psig. If only the top or low pressure disc is leaking during relief gas flow, the pressure between the two discs will be about 1 to 2 inches water gauge (almost 0 psig). If both discs are leaking during relief gas flow, this pressure between the two discs will be about 5 psig (about the pressure in the drop-out drum) and flow can by-pass the acid relief neutralizer, in part.

When the acid relief neutralizer cannot allow flow of relief gases therethrough, for example liquid hydrocarbon, e.g., propane, enters the acid relief neutralizer and vaporizes causing refrigeration and freeze-up in the system, then pressure starts to build up in the acid relief neutralizer and in the drop-out drum. When pressure reaches 50 psia (the rupture pressure for the high pressure rupture disc) both discs will rupture, and the relief gases by-pass the acid relief neutralizer, allowing the operator to correct the problem to bring the unit back to proper operating conditions, after which, two new relief or rupture discs are installed.

The system allows for venting cleaned (HF-free) gases to the flare via the acid relief neutralizer; indicates if either or both of the discs are leaking (which could by-pass HF-containing fluid to the flare—HF remaining as HF in the exhaust or flare combustion gases), so that the discs can be replaced with proper discs; and sweeps the system with inert gas (nitrogen or sweet fuel gas) when no relief gases are flowing.

It is pointed out that the caustic solution is always flowing through the acid relief neutralizer whether or not relief gases are flowing. This caustic is kept warm, but even this heating system can fail.

We claim:
1. A handling system for acid-containing hydrocarbon vapor mixtures, said system comprising in combination:
   (a) a liquid knock-out vessel means,
   (b) means for introducing an acid-containing hydrocarbon vapor mixtures into said liquid knock-out vessel means,
   (c) means to remove liquid from said liquid knock-out vessel means,
   (d) a neutralizing vessel means,
   (e) means to remove acid-containing vapor from said liquid knock-out vessel means and to pass same to said neutralizing vessel means,
   (f) means for removing neutralizing agent from a lower portion of said neutralizing vessel means and to pass same to an upper portion of said neutralizing vessel means, said agent removing means being provided with a heating means to heat circulating neutralizing agent,
   (g) means for removing de-acidified vapors from an upper portion of said neutralizing vessel means and for passing same to a flare,
   (h) safety by-pass means connecting said liquid knock-out vessel means and said flare, said by-pass means being provided with a high pressure rupture disc in close proximity to said liquid knock-out vessel means and a low pressure rupture disc downstream from said high pressure rupture disc and located between said high pressure disc and said flare, and
   (i) means for introducing a sulfur-free and HF-free purge gas into a by-pass line forming part of said safety by-pass means and which is in open communication with the downstream portion of said low pressure rupture disc, means for maintaining open pressure communication between said purge gas introduction means and the upstream portion of said low pressure rupture disc and with the downstream portion of said high pressure rupture disc for introducing purge gas therebetween, said by-pass means affording a vapor relief safety by-pass for said liquid knock-out vessel means when both said high pressure rupture disc and said low pressure rupture disc are ruptured by excessive pressure in the liquid knock-out vessel means.

2. A system according to claim 1 wherein measuring means are provided to measure the gas pressure differential between the upstream portion of said low pressure rupture disc and the downstream portion of said high pressure rupture disc for indicating whether either one or both of said rupture discs are leaking or are intact.

3. A system according to claim 1, wherein each said purge gas introduction means and said open communication means are provided with check valves to prevent backflow into said respective means during excessive vapor flow through said safety by-pass means during upset of the stream, and/or when said vapor mixture is entering said liquid knock-out vessel means.

4. A system according to claim 1 wherein said heating means is controlled responsive to the temperature is said neutralizing vessel means.

5. A system according to claim 1 including means for withdrawing liquid from said liquid-knock-out vessel means and connected to a storage vessel provided with means to remove liquid from a lower portion thereof, and means connecting an upper vapor portion of said storage vessel with said by-pass line at a location downstream of said low pressure rupture disc.

6. A system according to claim 5 further including check valve means in said liquid withdrawing means at a location between said liquid knock-out vessel means and said storage vessel to prevent backflow to said liquid knock-out vessel means.

* * * * *